(12) United States Patent
Tranvouez-Bernardin et al.

(10) Patent No.: US 11,402,661 B2
(45) Date of Patent: Aug. 2, 2022

(54) METHOD FOR DETERMINING AN OPHTHALMIC LENS ADAPTED TO A LOCOMOTION PARAMETER

(71) Applicant: Essilor International, Charenton-le-Pont (FR)

(72) Inventors: Delphine Tranvouez-Bernardin, Charenton-le-Pont (FR); Konogan Baranton, Charenton-le-Pont (FR); Isabelle Poulain, Charenton-le-Pont (FR); Laurent Calixte, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 44 days.

(21) Appl. No.: 16/085,362

(22) PCT Filed: Mar. 9, 2017

(86) PCT No.: PCT/EP2017/055578
§ 371 (c)(1),
(2) Date: Sep. 14, 2018

(87) PCT Pub. No.: WO2017/157760
PCT Pub. Date: Sep. 21, 2017

(65) Prior Publication Data
US 2019/0113770 A1    Apr. 18, 2019

(30) Foreign Application Priority Data
Mar. 15, 2016 (EP) .................................... 16305279

(51) Int. Cl.
*G02C 7/02* (2006.01)
*A61B 3/113* (2006.01)
(Continued)

(52) U.S. Cl.
CPC .............. *G02C 7/027* (2013.01); *A61B 3/113* (2013.01); *G02C 13/005* (2013.01); *G02C 7/061* (2013.01)

(58) Field of Classification Search
CPC ...... G02C 7/027; G02C 7/061; G02C 13/005; G02C 7/02; G02C 7/022; G02C 7/028;
(Continued)

(56) References Cited

U.S. PATENT DOCUMENTS

| 6,655,803 | B1 * | 12/2003 | Rubinstein ............. G02C 7/028 |
| | | | 351/159.74 |
| 8,079,705 | B2 * | 12/2011 | Drobe ...................... G02C 7/02 |
| | | | 351/159.8 |
| 2007/0229761 | A1 | 10/2007 | Gimenez Carol et al. |
| 2009/0248377 | A1 | 10/2009 | Shinohara et al. |

(Continued)

FOREIGN PATENT DOCUMENTS

| CN | 104380179 A | 2/2015 |
| CN | 105026989 A | 11/2015 |

(Continued)

OTHER PUBLICATIONS

International Search Report dated Jun. 22, 2017, in PCT/EP2017/055578, filed Mar. 9, 2017.

*Primary Examiner* — Travis S Fissel
(74) *Attorney, Agent, or Firm* — Oblon, McClelland, Maier & Neustadt, L.L.P.

(57) ABSTRACT

A method for determining an ophthalmic lens adapted to a wearer, including: providing wearer data including at least an indication of a prescription of the wearer; providing a locomotion scenario including at least an input locomotion parameter and visual environment data indicative of a visual environment, the locomotion parameter including at least movement data indicative of at least translation movements of the wearer's head; providing an output parameter of a locomotion parameter of the wearer or an optical parameter of the ophthalmic lens having an impact on a locomotion
(Continued)

parameter of the wearer; determining an ophthalmic lens adapted to the wearer based at least on the wearer data to have the output parameter as close as possible to the target value of the output parameter when carrying out the locomotion scenario using the ophthalmic lens, wherein the output parameter is retinal flow of the wearer.

14 Claims, 10 Drawing Sheets

(51) Int. Cl.
  *G02C 13/00* (2006.01)
  *G02C 7/06* (2006.01)
(58) Field of Classification Search
  CPC ........ G02C 7/063; G02C 7/065; G02C 7/066; A61B 3/113
  USPC .......................... 351/159.01, 159.73, 159.74
  See application file for complete search history.

(56) References Cited

U.S. PATENT DOCUMENTS

| | | | |
|---|---|---|---|
| 2010/0214531 A1* | 8/2010 | Suzuki | G02C 7/027 351/159.75 |
| 2011/0128496 A1* | 6/2011 | Giraudet | G02C 7/027 351/204 |
| 2011/0222019 A1 | 9/2011 | Suzuki et al. | |
| 2015/0051508 A1 | 2/2015 | Ghajar et al. | |
| 2015/0124214 A1 | 5/2015 | Contet et al. | |
| 2015/0286070 A1 | 10/2015 | Aikawa | |
| 2016/0011437 A1 | 1/2016 | Nishimura et al. | |
| 2016/0026001 A1 | 1/2016 | Nishimura et al. | |
| 2017/0090220 A1 | 3/2017 | Bonnin et al. | |

FOREIGN PATENT DOCUMENTS

| | | |
|---|---|---|
| EP | 1 747 750 A1 | 1/2007 |
| EP | 2 105 088 A1 | 9/2009 |
| EP | 2 899 585 A1 | 7/2015 |
| JP | 2006-72192 A | 3/2006 |
| WO | WO 2015/177459 A1 | 11/2015 |

* cited by examiner

METHOD FOR DETERMINING AN OPHTHALMIC LENS ADAPTED TO A LOCOMOTION PARAMETER

FIELD OF THE INVENTION

The invention relates to a method for determining an ophthalmic lens adapted to a wearer based on the prescription of the wearer and at least a locomotion parameter of the wearer.

BACKGROUND OF THE INVENTION

Usually, a person needing to wear spectacles and having thus a prescription filled by an ophthalmologist or optometrist goes to the shop of an optician. The optician orders a pair of optical lenses corresponding to the prescription of the wearer.

The pair of optical lenses sent to the optician are designed and manufactured according to optical criteria determined based on the prescription of the wearer.

Recent improvements in the field of ophthalmic lenses, have allowed providing customized optical lenses, such customization going beyond the wearer's prescription. Further parameters than the wearer's prescription may be considered when designing and manufacturing the pair of ophthalmic lenses.

To meet new needs or specifications of the wearer, methods of optimization of optical lenses depending on the setting of segmentation/customization are usually used.

Usually, the prescription of the wearer is determined in a static state and the optical design of the spectacle lenses to be provided to the wearer is determined considering a static visual target.

However, most of the time when a wearer is using the spectacle lenses he or she is moving relative to the visual environment.

Therefore, there is a need for a method for determining an ophthalmic lens that would be adapted to the fact that the wearer is actually moving most of the time when using the ophthalmic lens.

One object of the present invention is to provide a new method for determining an ophthalmic lens adapted to a wearer considering the locomotion of the wearer when wearing the ophthalmic lenses.

SUMMARY OF THE INVENTION

To this end, the invention proposes a method, for example implemented by computer means, for determining an ophthalmic lens adapted to a wearer, the method comprising:
  a wearer data providing step, during which wearer data comprising at least an indication of the prescription of the wearer are provided,
  a locomotion scenario providing step during which a locomotion scenario is provided, the locomotion scenario comprising at least an input locomotion parameter and visual environment data indicative of a visual environment, the locomotion parameter comprising at least movement data indicative of at least a translation movement of the head of the wearer upon movement in a visual environment,
  an output parameter providing step during which a target value of an output parameter is provided, the output parameter being a locomotion parameter of the wearer or an optical parameter of the ophthalmic lens having an impact on a locomotion parameter of the wearer,
  an ophthalmic lens determining step, during which an ophthalmic lens adapted to the wearer is determined based at least on the wearer data so as to have the output parameter as close as possible to the target value of the output parameter when carrying out the locomotion scenario using the ophthalmic lens.

Advantageously, the method of the invention allows determining the ophthalmic lens adapted to a wearer based at least on the prescription of the wearer and a locomotion parameter of the wearer. Therefore, the ophthalmic lens determined by the method of the invention is more adapted to the movements of the wearer.

According to further embodiments which can be considered alone or in combination:
  the input locomotion parameter is a parameter of the wearer when carrying out the locomotion scenario using the ophthalmic lens; and/or
  the locomotion parameter is the trajectory and/or the speed and/or the direction and/or the movements of any part of the body, for example the head, and/or the eye direction and/or the eye movements and/or the stability and/or the yaw and/or the pitch and/or the roll and/or the bounce and/or the sway of the wearer when carrying out the locomotion scenario using the ophthalmic lens; and/or
  the ophthalmic lens comprises a zone of optical interest and during the ophthalmic lens determining step the optical function of at least a first part of the zone of optical interest is determined based at least on the output parameter and the prescription of the wearer; and/or
  the optical function of at least a second part of the zone of optical interest is determined without considering the locomotion parameter; and/or
  the dimensions and/or the position of the first part of the zone of optical interest are determined based on the locomotion scenario and/or wearer personalization data relating indicative of at least to the age and/or the morphology and/or the sensory motor state of the wearer; and/or
  the ophthalmic lenses determining step further comprises a optical function selecting step during which an optical function is selected in a list consisting of at least two optical functions, the optical function being selected based at least on the wearer data; and/or
  the wearer data further comprise a troubling output parameter and during the optical function selecting step an optical function is selected so as to minimize the troubling output parameter when carrying out the locomotion scenario using the ophthalmic lens; and/or
  the locomotion parameter of the wearer is measured using a sensing device carried by the wearer upon movement in the visual environment; and/or
  the locomotion parameter of the wearer is determined based on a statistic model of an average wearer, for example from a database; and/or
  the ophthalmic lenses determining step further comprises a geometry determining step during which geometrical parameter of the ophthalmic lens are determined, the geometrical parameters being determined based at least on the wearer data; and/or
  the ophthalmic lenses determining step further comprises:
    a set of parameters providing step, during which a set of parameters of the ophthalmic lens is provided, the set of parameter comprising at least an output parameter of the wearer when carrying out a locomotion scenario using the ophthalmic lens, a set of cost functions providing step during which for each parameter of the set of parameter a cost function is provided, during the ophthalmic lens determining step the ophthalmic lens is determined so as to minimize the global cost function the global cost function being a weighted sum of the cost functions; and/or the output parameter is the retinal flow of the wearer when carrying out the locomotion scenario using the ophthalmic lens; and/or the visual environment and the ophthalmic lens are virtually simulated; and/or the wearer is virtually simulated.

The invention further relates to a computer program product comprising one or more stored sequences of instructions that are accessible to a processor and which, when executed by the processor, causes the processor to carry out the steps of the method according to the invention.

The invention also relates to a computer-readable storage medium having a program recorded thereon; where the program makes the computer execute the method of the invention.

The invention further relates to a device comprising a processor adapted to store one or more sequence of instructions and to carry out at least one of the steps of the method according to the invention.

Unless specifically stated otherwise, as apparent from the following discussions, it is appreciated that throughout the specification discussions utilizing terms such as "computing", "calculating", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. This apparatus may be specially constructed for the desired purposes, or it may comprise a general purpose computer or Digital Signal Processor ("DSP") selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

The processes and displays presented herein are not inherently related to any particular computer or other apparatus. Various general purpose systems may be used with programs in accordance with the teachings herein, or it may prove convenient to construct a more specialized apparatus to perform the desired method.

The desired structure for a variety of these systems will appear from the description below. In addition, embodiments of the present invention are not described with reference to any particular programming language. It will be appreciated that a variety of programming languages may be used to implement the teachings of the inventions as described herein.

BRIEF DESCRIPTION OF THE DRAWINGS

Embodiments of the invention will now be described, by way of example only, and with reference to the following drawings in which.

DETAILED DESCRIPTION OF PREFERRED EMBODIMENTS

The invention relates to a method, for example implemented by computer means, for determining an ophthalmic lens adapted to a wearer.

Figure 1:
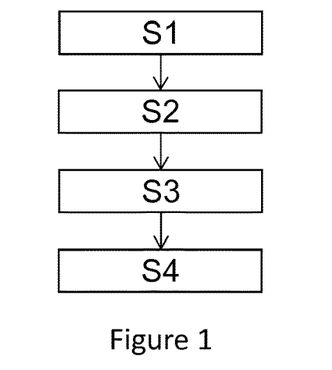
FIG. 1 is a flowchart of the steps of a method according to the invention.

As illustrated on FIG. 1, the method according to the invention comprises at least:
a wearer data providing step S1,
a locomotion scenario providing step S2,
an output parameter providing step S3, and
an ophthalmic lens determining step S4.

During the wearer data providing step S1, wearer data comprising at least an indication of the prescription of the wearer are provided.

In the sense of the invention, the prescription is a set of optical characteristics of optical power, of astigmatism and, where relevant, of addition, determined by an ophthalmologist in order to correct the vision defects of an individual, for example by means of a lens positioned in front of his eye. Generally speaking, the prescription for a progressive addition lens comprises values of optical power and of astigmatism at the distance-vision point and, where appropriate, an addition value.

During the locomotion scenario providing step S2 a locomotion scenario is provided.

The locomotion scenario comprises at least visual environment data indicative of a visual environment.

The visual environment data may be indicative of structure, texture of the world and objects, light atmosphere, spatial frequencies, presence of objects, people, etc. . . .

The visual environment may be a real word environment or a virtually simulated environment.

When the visual environment is a real word environment, the visual environment data may be measured by sensors either worn by the wearer or placed in the environment.

For example, according to an embodiment of the invention, the locomotion parameter of the wearer is measured using a sensing device carried by the wearer upon movement in the visual environment.

When the visual environment is a virtual simulated visual environment, the visual environment data may be at least part of the data defining the virtual simulated visual environment.

The locomotion scenario further comprises at least an input locomotion parameter comprising at least movement data indicative of at least a translation movement not null, of the head of the wearer upon movement in a visual environment.

The locomotion parameters may comprise wearer's movement features such as trajectory, speed, directions and movements of any part of the body, for example of the head, such as rotations and translations of head, directions and eye movements (gazing down, eccentricity . . . ), how to cross an obstacle for example raising the foot, the yaw, pitch, roll, bounce and sway, segmental and oculomotor coordination (Vestibulo-Ocular Reflex, anchoring index), the stability of the body during walking . . . .

The locomotion scenario may further comprise indication concerning the type of movement of the wearer in the visual environment for example driving, walking, bicycling, running, going up or down the stairs.

Preferably, the input locomotion parameter is a locomotion parameter of the wearer when carrying out the locomotion scenario using an ophthalmic lens.

During the output parameter providing step S3 a target value of an output parameter is provided. The output parameter may be a locomotion parameter of the wearer or an optical parameter of the ophthalmic lens having an impact on a locomotion parameter of the wearer.

According to an embodiment of the invention, the locomotion parameter may be selected in the list consisting of the trajectory, the speed, the direction of the head or any other parts of the body of the wearer, head movements, the eye gazing direction, the eye movements, the stability, the yaw, the pitch, the roll, the bounce, the sway of the wearer when carrying out the locomotion scenario using the ophthalmic lens.

Locomotion parameter may be defined as any parameter characterizing the movement of the wearer or perceptual parameter related to a locomotion task such as the perceived speed of movement of objects, the optical flow, the perception an obstacle located on the ground, the perception of vertical, horizontal, perception of the slopes, the sensation of pitching, depth perception, perception of absolute or relative objects distances . . . .

Optical parameter may be defined as a parameter that may be calculated by ray tracing through the ophthalmic lens, such as power profile of the meridian, widths of iso power or astigmatism lines fields, power or astigmatism gradients, wavefront, optical flow, retinal flow, deviation maps etc. . . .

Optical parameter may be defined within the framework of the invention as long as it has an impact on sensorimotor behavior or perception of the wearer when moving. Defining at least one optical parameter requires at least the definition of a locomotion scenario. The various locomotion scenario parameters may influence the selection of at least one optical parameter.

The optical flow can be considered both as a locomotion parameter, it characterizes the direction and speed of movement of the wearer in the case, for example, recording the streams over a scene camera and an optical parameter, in this case it is the optical flow calculated by ray tracing through the ophthalmic lens.

The wearer perceives the features of his own movement via visual information such as optic flow. The optical flow is characterized by optical changes produced by the relative movement of the wearer's head in the environment. Retinal flow corresponds to a projection of optical flow in retinal coordinates on the receiving surface. It is affected by the viewing direction and rotation of the eye in the orbit. The retinal flow is usually represented by a vector field. Each vector of the field corresponds to a speed and a direction of movement of an element of the environment. The combination of body movements, eyes and depth of objects in the visual environment then determine the structure of the optical flow on the retina (Callow and Lappe (2007) Local statistics of retinal optic flow for self-motion through natural sceneries).

Retinal flow induced by a moving wearer depends on the speed and direction of movement of the head of the wearer, the rotation of his eyes and the composition of the environment (structure, object distance . . . ). In the case of a pure translation movement of a moving subject on a straight path forward and looking in the direction of its movement, retinal flow matching is a purely radial expansion flow. Mostly the retinal flow combines components in translation and rotation. When the wearer is wearing an ophthalmic lens the retinal flow also depends on the features of the ophthalmic lens, in particular the optical function of the ophthalmic lens.

The choice of locomotion and/or optical criteria may be dictated by wearer parameters such as age, activities (schedule activities for example), ametropia etc. . . .

For example, the locomotion scenario may be the displacement of the body. The visual environment is the ground texture in front of the wearer. The displacement of the body is maintained stable when visual cues are available and reliable two steps ahead. The visibility window of the ground two steps ahead projected on the lenses defined the dimensions and location of a first part of the zone of optical interest. Inside this first part of the zone of optical interest, an output parameter is defined as the depth cues. A target value of this output parameter is the depth cues values computed with a reference lens. The optimization will consist to minimize the deviation between the target value and the depth cues values computed with the ophthalmic lens while determining it.

According to an embodiment of the invention, the method of the invention may be used to determine the most appropriate optical design for a progressive ophthalmic lens. In particular, the optical design that provides a retinal flow as close as possible to the retinal flow of a single vision plano ophthalmic lens.

Figure 3:
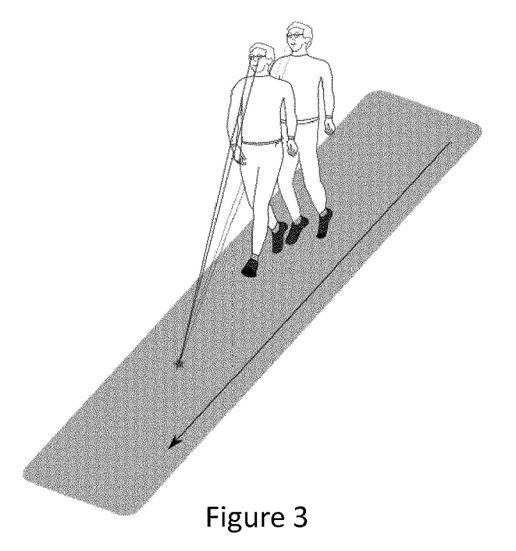
FIG. 3 illustrates an example of locomotion scenario in an embodiment of the invention.

As illustrated on FIG. 3, in such example, the locomotion scenario is the wearer walking without moving his head and gazing at a point on the ground. The input locomotion parameters in this example comprise the trajectory, the oculomotor direction, the visual environment such as the ground and wall.

Specifically, the movement is translational forward on a ground consisting of a grid according to an axis perpendicular to a vertical grid. In the initial position the wearer is 5 m from the vertical grid and the center of rotation of the wearers eyes are 1 m70 from the ground. The wearer looks at a point on the ground.

The output locomotion parameter is the retinal flow of the wearer wearing ophthalmic lenses. The retinal flow is calculated between the initial position of the wearer and a final position located 25 cm away. The target value is the retinal flow of the wearer when wearing single vision plano ophthalmic lens.

In this example, the inventors have observed that the most relevant is to focus on the peripheral part of the retina flow, i.e. in the temporal and nasal areas.

Figure 4A:
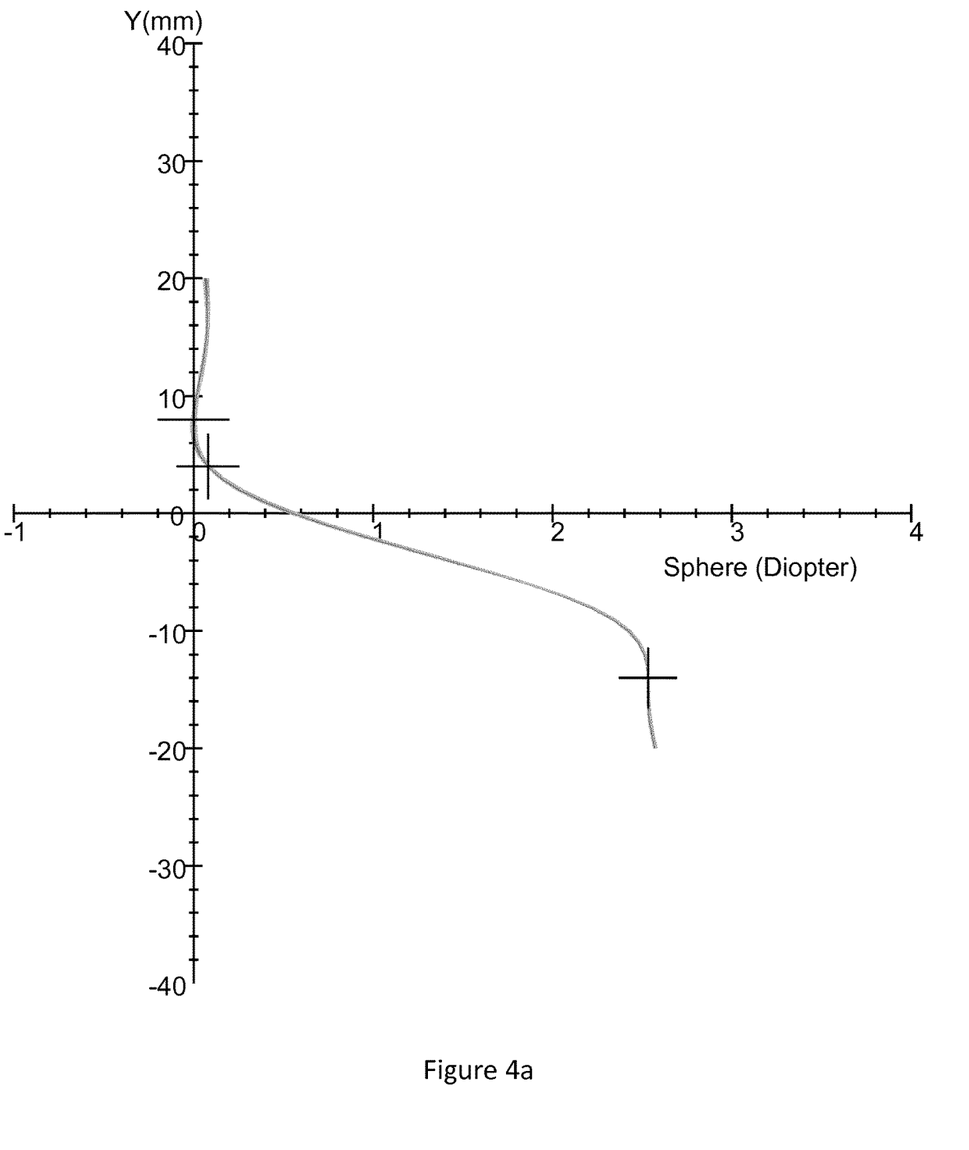
FIGS. 4 to 7 illustrate an example of implementation of the method of the invention.
Figure 4B:
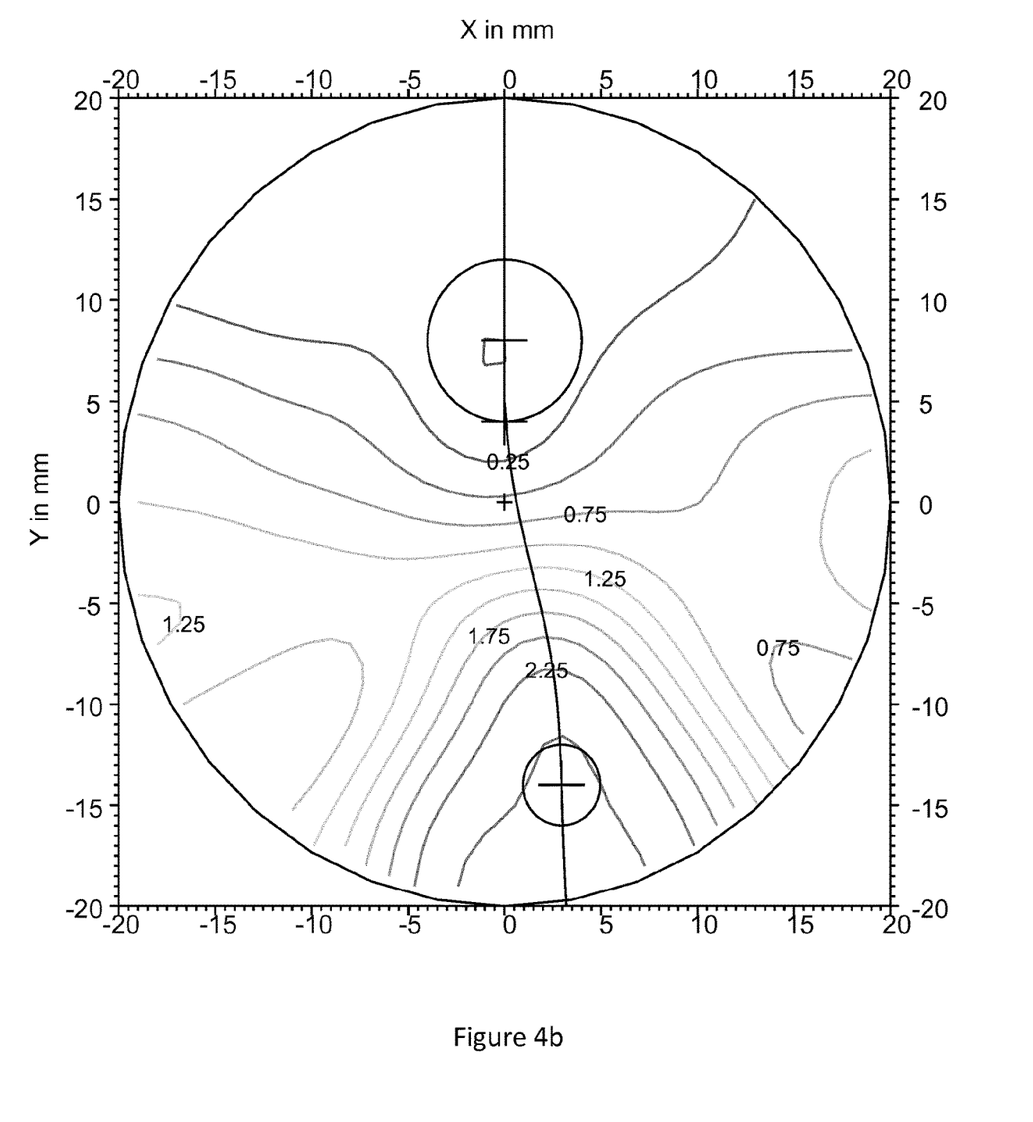
Figure 4C:
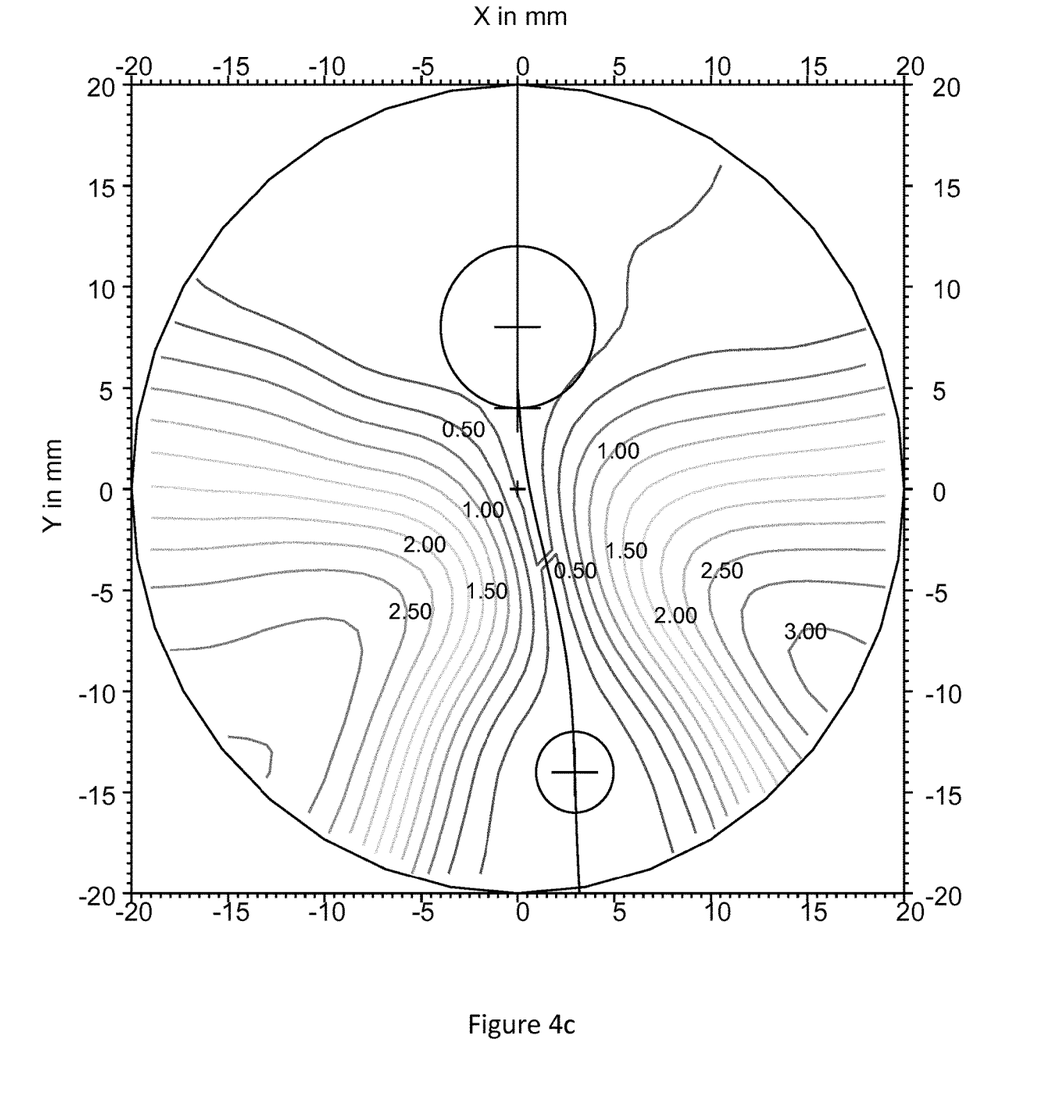

The first progressive design EI1 corresponds to an ophthalmic lens with an addition of 2.5 D, a far vision prescription of 0 D and adapted for a head/eye movement coefficient of 0. FIGS. 4a to 4c show features of the front surface of such an ophthalmic lens having the first progressive design E1 and a refractive index of 1.665.

FIG. 4a shows mean sphere curve surrounded by minimum and maximum sphere curves, along the meridian. The x-axes are graduated in diopters, and the y-axes give the height, in mm, on the lens.

FIG. 4b shows lines of equal mean sphere, i.e. lines formed by points for which the mean sphere has an identical value. The x-axis and y-axis give the coordinates in mm.

FIG. 4c shows, using the same axes as for FIG. 4b, lines of equal cylinder.

Figure 5A:
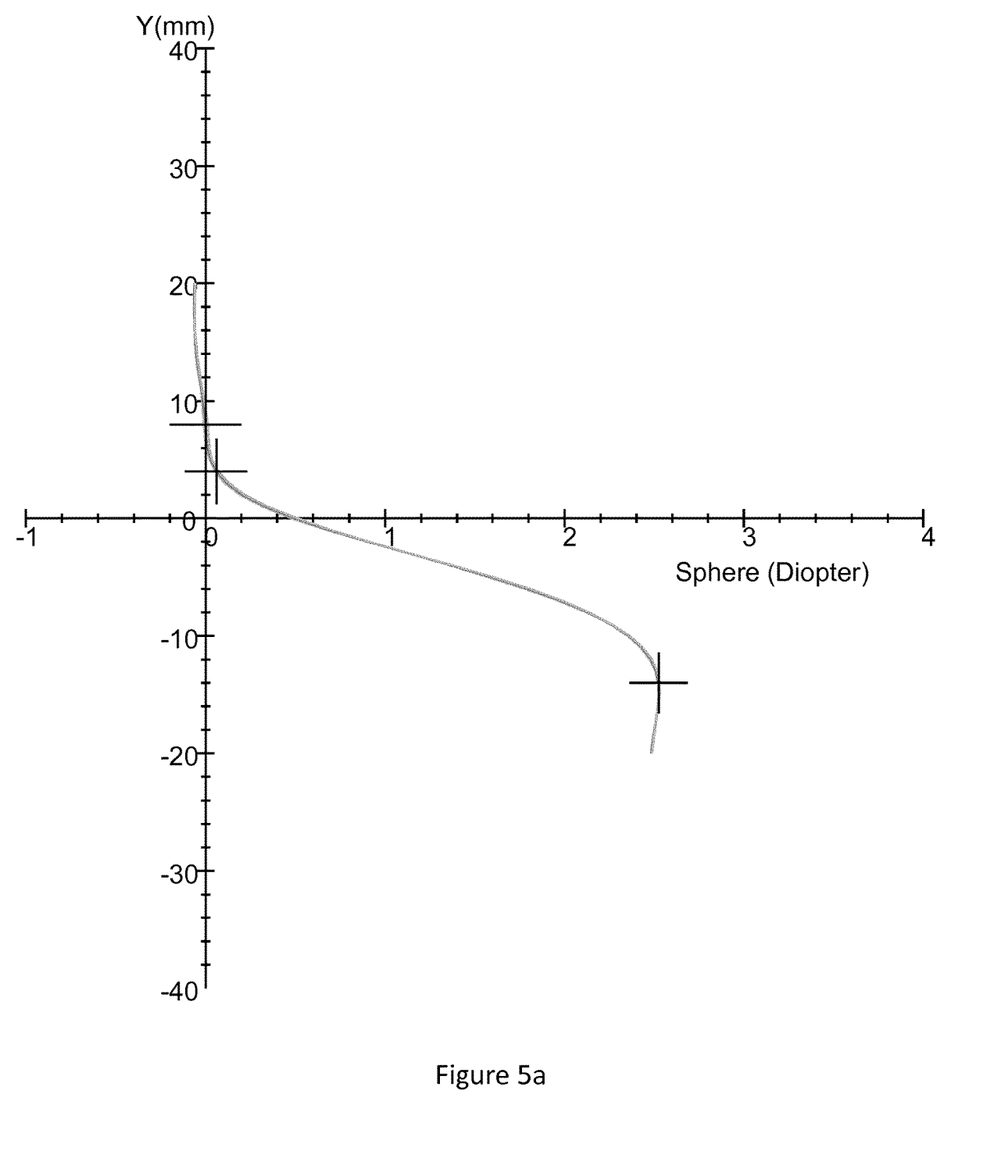
Figure 5B:
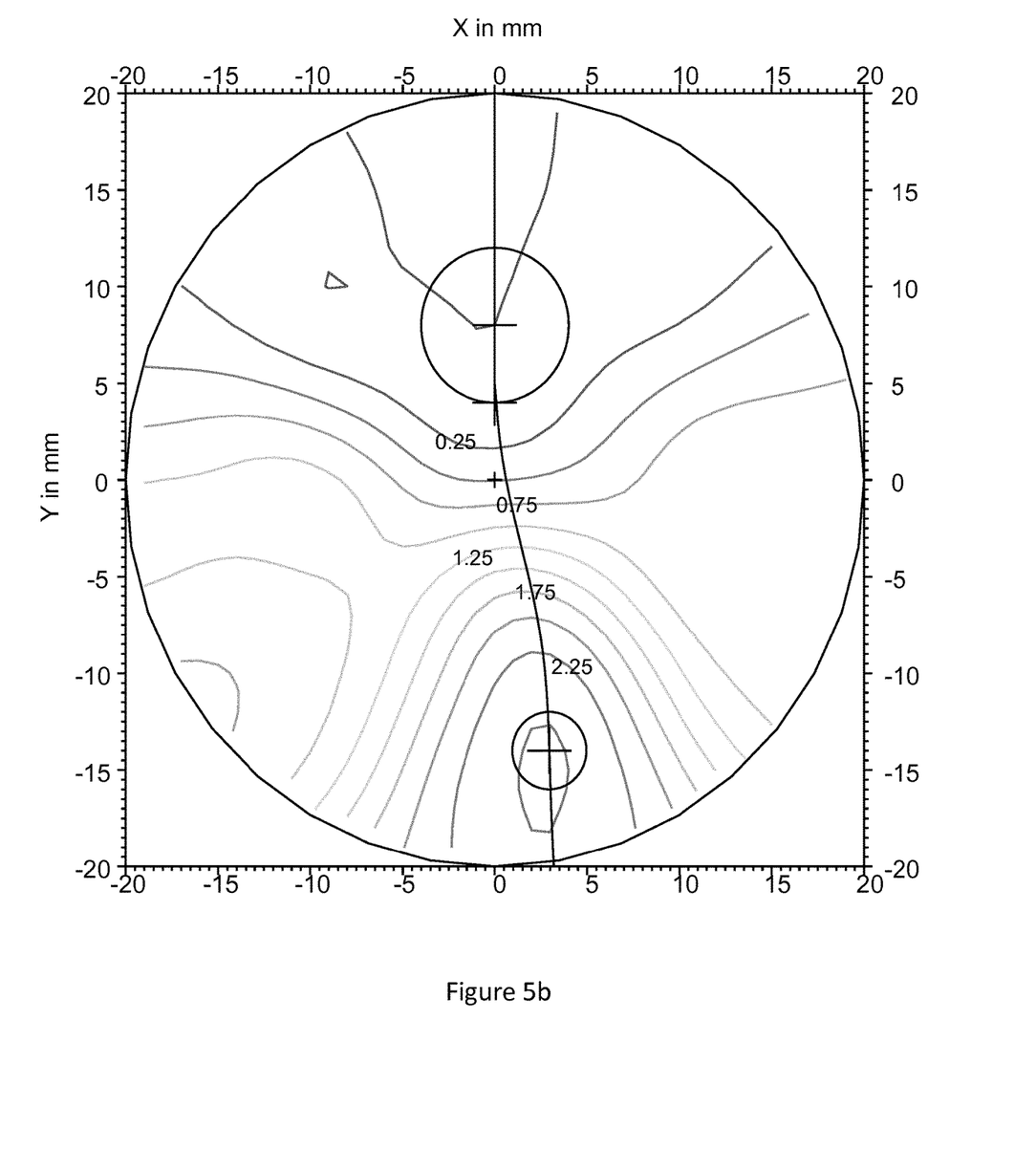
Figure 5C:
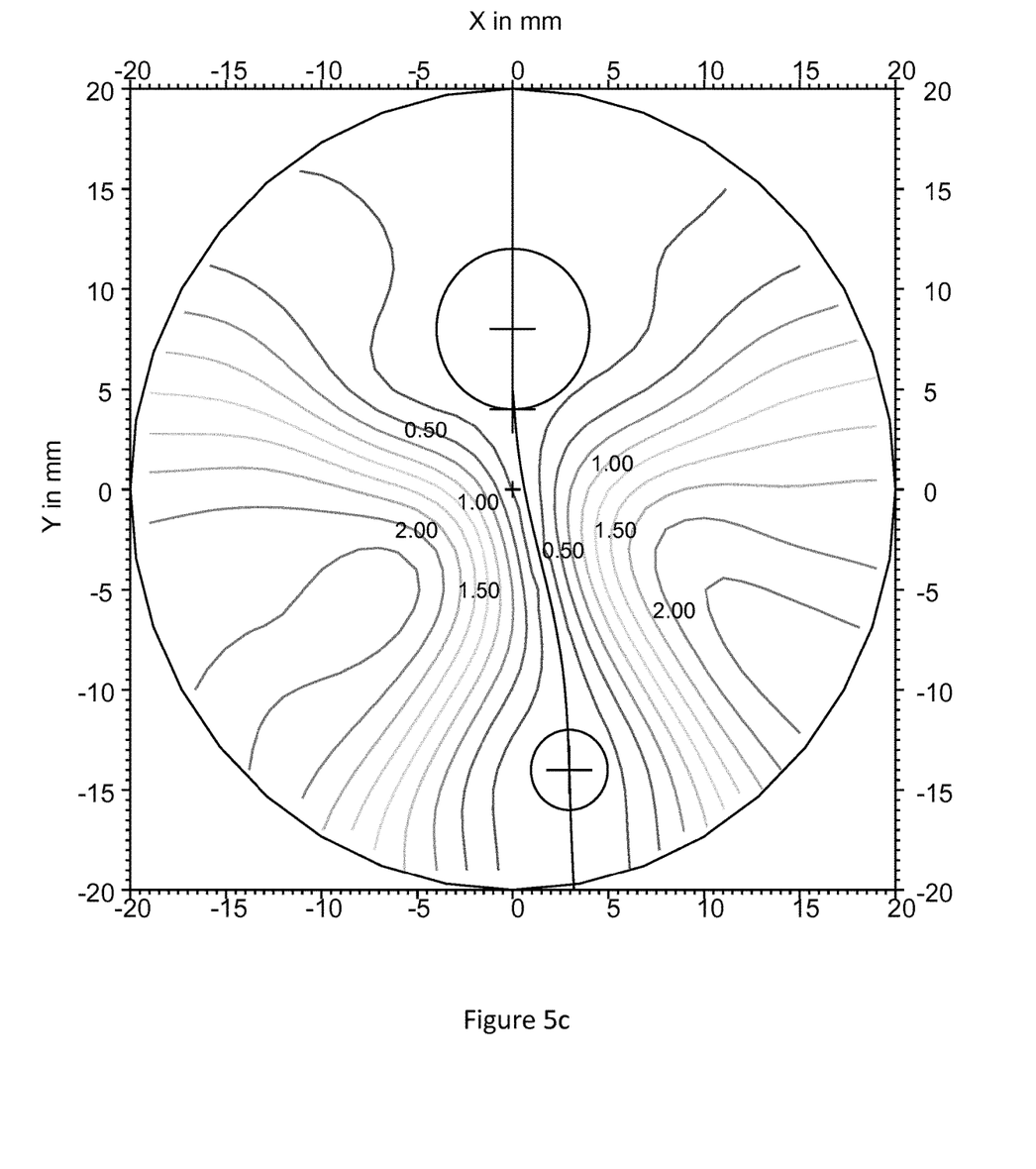

The second progressive design EI2 corresponds to an ophthalmic lens with an addition of 2.5 D, a far vision prescription of 0 D and adapted for a head/eye movement coefficient of 1. FIGS. 5a to 5c show features of the front surface of such an ophthalmic lens having the second progressive design E3 and a refractive index of 1.665.

FIG. 5a shows mean sphere curve surrounded by minimum and maximum sphere curves, along the meridian. The x-axes are graduated in diopters, and the y-axes give the height, in mm, on the lens.

FIG. 5b shows lines of equal mean sphere, i.e. lines formed by points for which the mean sphere has an identical value. The x-axis and y-axis give the coordinates in mm.

FIG. 5c shows, using the same axes as for FIG. 5b, lines of equal cylinder.

Figure 6A:
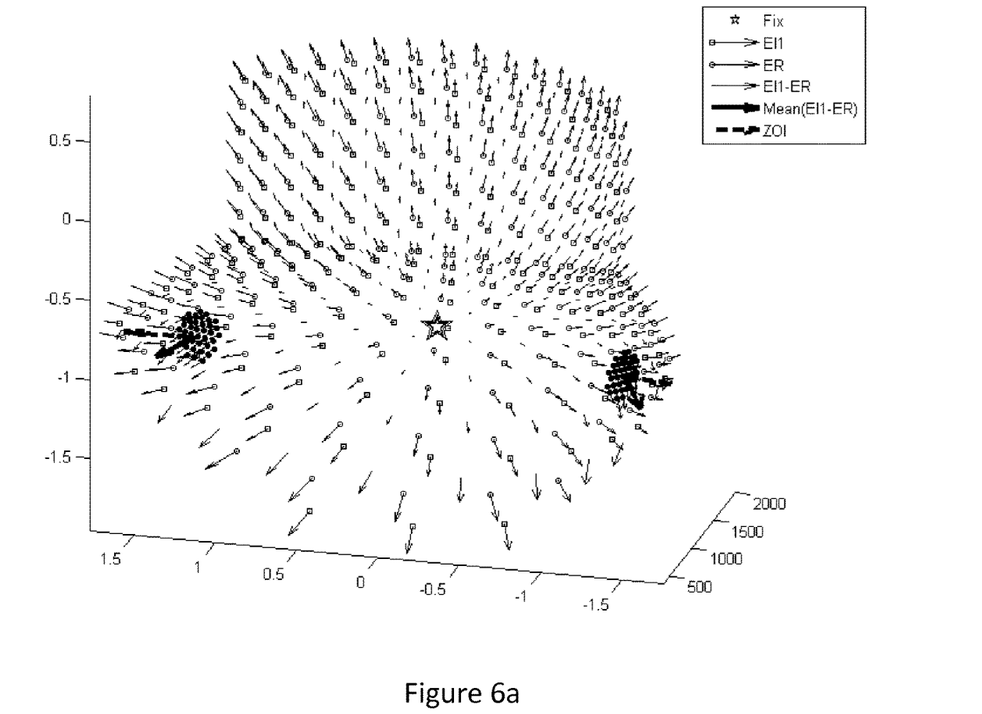

FIG. 6a illustrates the comparison of the retinal flow with the single vision design, represented by the arrows starting with a circle, and the retinal flow with the first progressive design EI1 represented by the arrows starting with a circle.

Figure 6B:
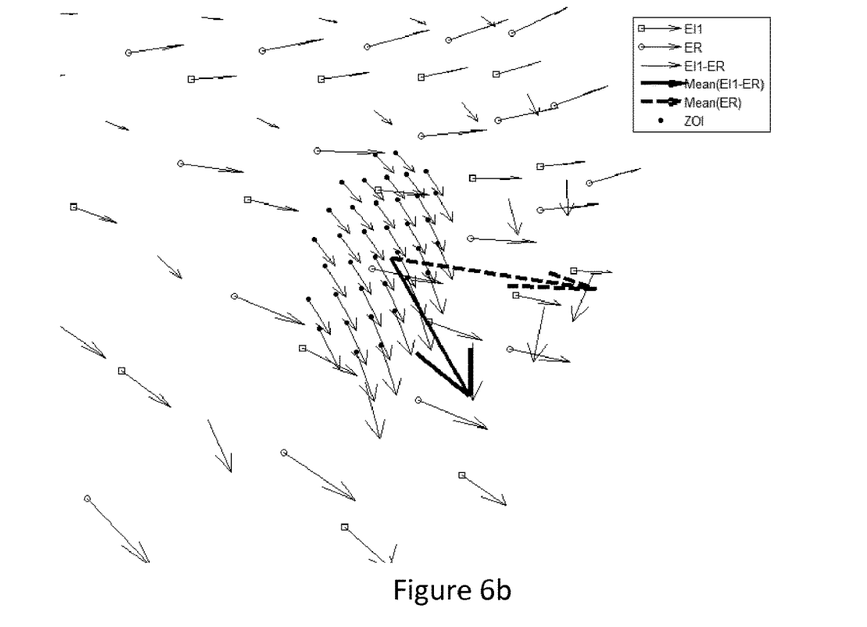
Figure 6C:
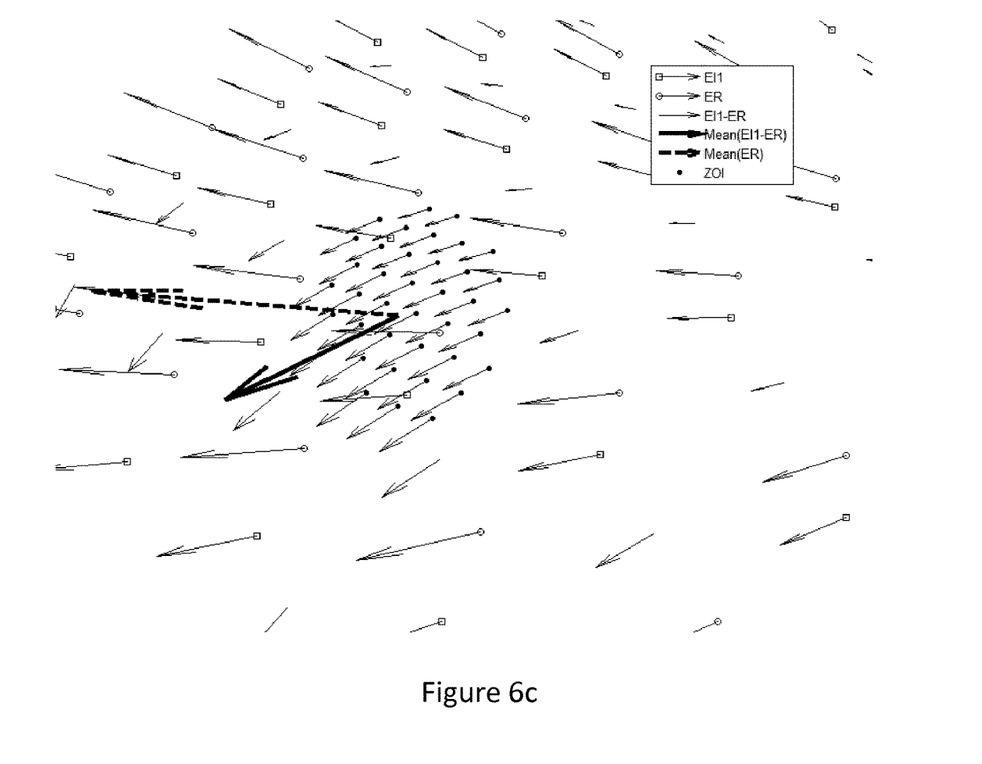

FIGS. 6b and 6c represent focus respectively on the nasal and temporal areas of FIG. 6a.

Figure 7A:
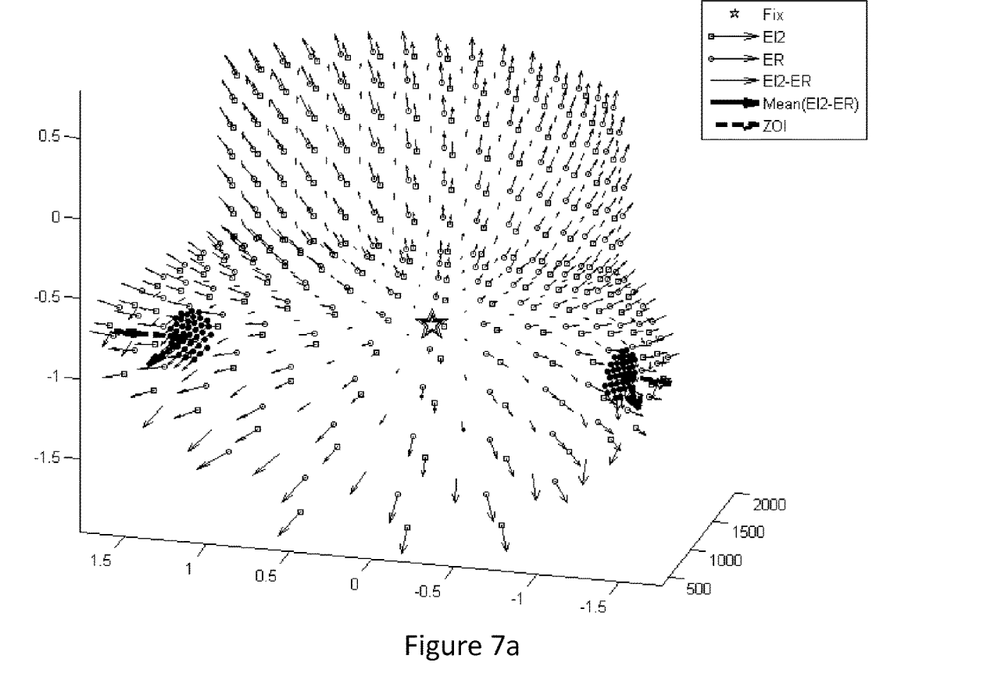

FIG. 7a illustrates the comparison of the retinal flow with the single vision design, represented by the arrows starting with a circle, and the retinal flow with the second progressive design EI2 represented by the arrows starting with a square.

Figure 7B:
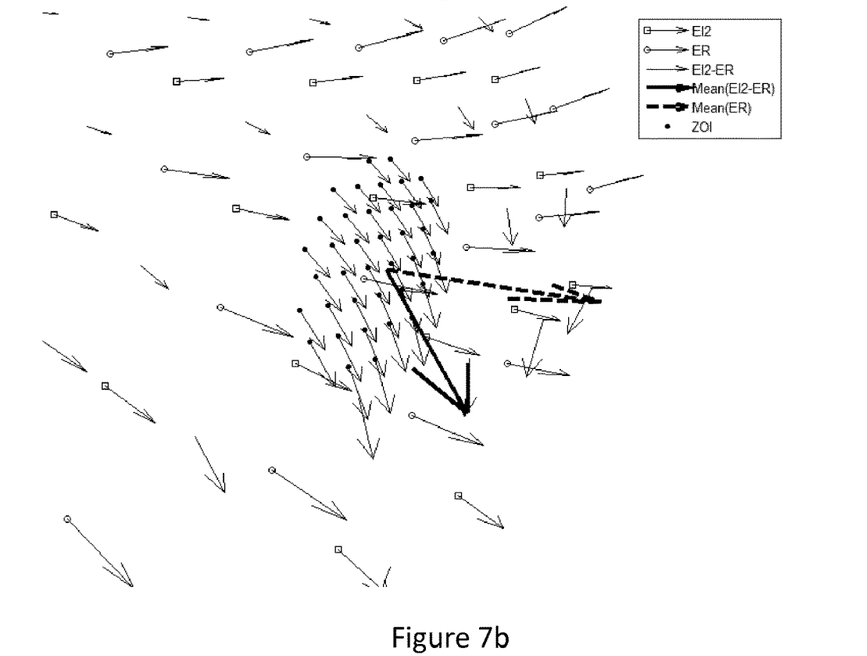
Figure 7C:
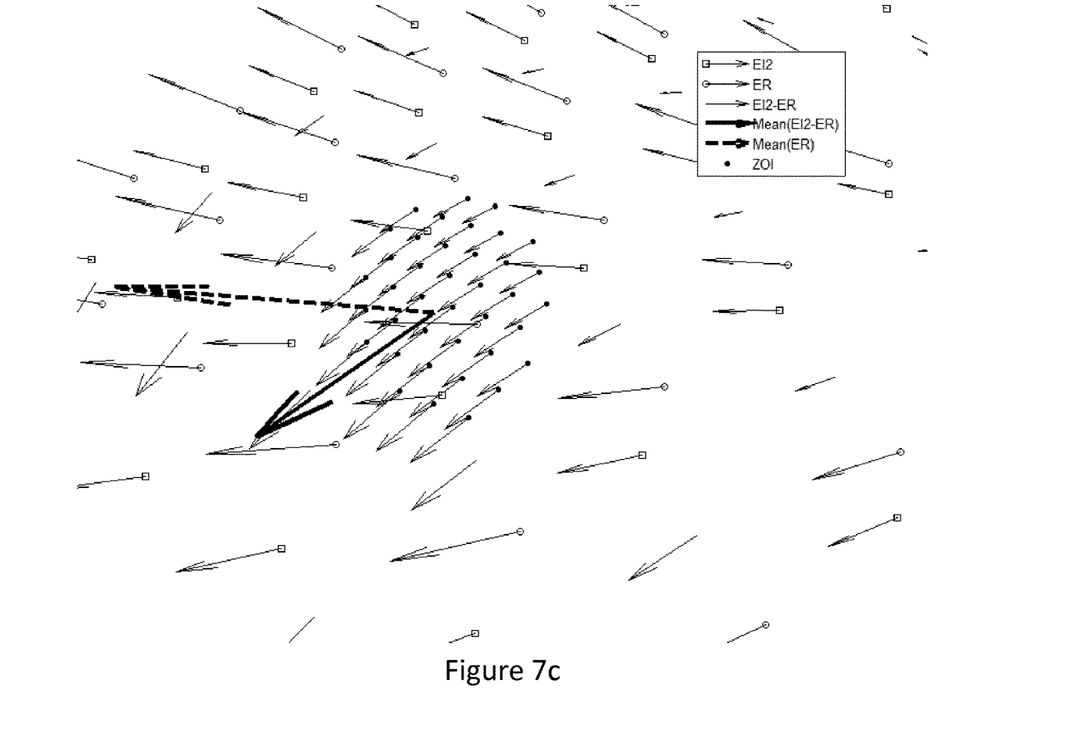

FIGS. 7b and 7c represent focus respectively on the nasal and temporal areas of FIG. 7a.

On FIGS. 6a and 6b the point of fixation is represented by a star.

The single arrows represent the differences between the retinal flow with the single vision design and the progressive designs. The differences of retinal flow, single arrows, between the single vision and the two progressive designs are measured more specifically in the two areas of interest, i.e. temporal and nasal areas, on flow charts expressed in the retinal reference and projected onto a sphere of 2 meters radius centered on the cyclopean eye of the wearer.

For each progressive design, resultant vectors, represented as a solid arrows on FIGS. 6b, 6c, 7b and 7c corresponding to the difference between the average of progressive design optic flow and the average of single vision optic flow are determined for two areas (temporal and nasal) of the zone of optical interest.

For these two areas (temporal and nasal) of the optical zone of interest, the angle and amplitude ratio between the resultant and the target value single vision optic flow, represented as a dotted arrows on FIGS. 6b, 6c, 7b and 7c are calculated.

Table 1 summarizes the average values obtained.

TABLE 1

|  | EI1-ER | | EI2-ER | |
| --- | --- | --- | --- | --- |
|  | Temporal | Nasal | Temporal | Nasal |
| Angle | 30.5° | 30° | 36.5° | 30.1° |
| Amplitude ratio | 11.80% | 15.90% | 13.60% | 17.50% |

As illustrated in Table 1, the first progressive design E1 is the one having the smallest difference with the single vision ophthalmic lens for the retinal flow in peripheral vision and in the specific locomotion scenario. The wearer will be preferably proposed a lens having the first progressive design E1 instead of the second progressive design E2.

According to a further example of the invention, in the context of a sport, such as tennis, the locomotion parameter may relate to the movements of the body and/or head and/or eye of the wearer upon striking a ball, or when following the ball. The locomotion parameter may be related to the speed of the body or the head of the wearer to seek an ophthalmic lens that optimizes the speed of the wearer.

During the ophthalmic lens determining step an ophthalmic lens adapted to the wearer is determined. The ophthalmic lens is determined based at least on the wearer data and so as to have the output parameter as close as possible to the target value of the output parameter when carrying out the locomotion scenario using the ophthalmic lens.

Typically, the optical function and/or geometry of the ophthalmic lens is determined either by selection or by optimization.

In the sense of the invention, an optical function corresponds to a function providing for each gaze direction the effect of an ophthalmic lens on the light ray passing through the optical lens.

The optical function may comprise dioptric function, light absorption, polarizing capability, reinforcement of contrast capacity, etc. . . . .

The dioptric function corresponds to the optical lens power (mean power, astigmatism, the prismatic deviation, etc . . . ) as a function of the gaze direction.

The wording "optical design" is a widely used wording known from the man skilled in the art in ophthalmic domain to designate the set of parameters allowing defining a dioptric function of an ophthalmic lens; each ophthalmic lens designer has its own designs, particularly for progressive ophthalmic lenses. As for an example, a progressive ophthalmic lens "design" results of an optimization of a progressive surface so as to restore a presbyope's ability to see clearly at all distances but also to optimally respect all physiological visual functions such as foveal vision, extra-foveal vision, binocular vision and to minimize unwanted astigmatisms. For example, a progressive lens design comprises:
  a power profile along the main gaze directions (meridian line) used by the lens wearer during day life activities,
  distributions of powers (mean power, astigmatism, . . . ) on the sides of the lens, that is to say away from the main gaze directions.

According to an embodiment of the invention, an ophthalmic lens design that is adapted to a specific locomotion parameter.

According to an embodiment of the invention, the ophthalmic lens comprises a zone of optical interest and during the ophthalmic lens determining step the optical function of at least a first part of the zone of optical interest is determined based at least on the output parameter and the prescription of the wearer. For example, the optical function of at least a second part of the zone of optical interest is determined without considering the locomotion parameter.

For example the first part of the zone of optical interest may correspond to the visibility window of the ground two steps ahead projected on the lens.

The position and/or dimension of the first part and the second parts of the optical lens may be interdependent or independent.

In other words, the whole surface of the ophthalmic lens does not have to be considered when determining the optical design adapted to a locomotion parameter of the wearer.

The dimensions and/or the position of the first part of the zone of optical interest may be determined based on the locomotion scenario and/or wearer personalization data relating indicative of at least to the age and/or the morphology and/or the sensory motor state of the wearer.

As indicated previously, the ophthalmic lenses determining step S4 may comprises an optical function selecting step during which an optical function is selected in a list consisting of at least two optical functions, the optical function being selected based at least on the wearer data and the output parameter.

The optical function selecting step may be implemented by computer means or at least assisted by computer means for example, via a database or lookup table.

The optical function selecting step may also consists in having the wearer carry out the locomotion scenario using ophthalmic lenses having the different optical function of the list and measuring the output parameter to as to select the optical functions providing the output parameter as close as possible to the target value.

In the sense of the invention, the target value may correspond to:
  maximizing a locomotion parameter, for example maximizing movement speed,
  minimizing a locomotion parameter, for example the difference between the retinal flow and a reference retinal flow.
  reaching a threshold value, for example minimum safety distance between the foot of the wearer and the edge of the sidewalk,
  a defined value, for example having a target retinal flow of a single-focus lens of the same power.

The optical function determining step may be implemented using an optimization process.

Figure 2:
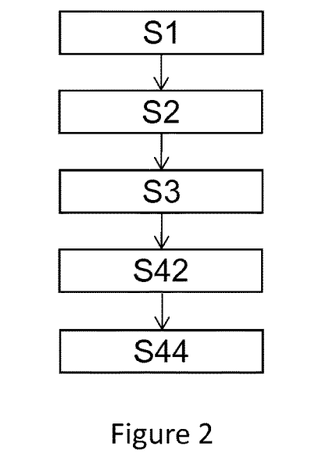
FIG. 2 is a flowchart of the steps of a method according to an embodiment of the invention.

For example as illustrated on FIG. 2, the ophthalmic lenses determining step of the method of the invention may further comprises:
  a set of parameters providing step S42, and
  a set of cost functions providing step S44.

During the set of parameters providing step S42 a set of parameters for optimizing the ophthalmic lens is provided. The set of parameter comprise at least an output parameter of the wearer when carrying out a locomotion scenario using the ophthalmic lens.

For each parameter of the set of parameter a cost function is provided during the set of cost functions providing step S44.

The ophthalmic lens is determined so as to minimize the global cost function, the global cost function being a weighted sum of the cost functions.

For example according to an embodiment of the invention, the first parameter may be the difference between the retinal flow with the ophthalmic lens and the retina flow of an ophthalmic lens of reference, such as a single vision ophthalmic lens. The second cost function may be the sum of the square difference over the first zone of optical interest of the lens for which we want the retinal flow to have the retina flow of the lens of reference.

A second parameter may be the difference between the prescription of the wearer and the power of the ophthalmic lens. The second cost function associated with this second parameter may be the sum of the square difference over a second zone of optical interest of the lens for which the prescription of the wearer has to be obtained.

The global cost function is the sum the first and second cost function and is minimized so that the above mentioned criteria are minimized.

According to an embodiment of the invention, the wearer data further comprise a troubling output parameter.

During the optical function determining step an optical function is selected so as to minimize the troubling output parameter when carrying out the locomotion scenario using the ophthalmic lens.

For example, a troubling output parameter may be related to "magnification", in particular in the lower part of the ophthalmic lens used by the wearer in locomotion situation. The troubling output parameter may relate to the maximum magnification in the lower part of the ophthalmic lens from which the stability of the wearer is degraded when walking.

An example of implementation of the method of the invention is provided.

When walking, the importance of the lower visual field was shown to maintain an efficient operation and to anticipate the obstacles on the ground. This anticipation visibility window of visual information is to be preserved. The deformations of the environment observed in this visibility window with a progressive lens are troublesome.

There is therefore a need to determine an ophthalmic lens limiting such troublesome. The method of the invention may be used to determine an ophthalmic lens that eliminates the problems of distortion and blurring associated with the near vision area while the wearer is moving.

A modification of the optical design may be combined with a calculation of power distribution in the lens adapted to a specific environment or a specific locomotion activity, but also a management/change of optical aberrations, an optical function (power, astigmatism), aesthetic criteria, linked to distortion, etc. . . . This can be for example:
  by using a cost function integrating these different types of criteria and assessing the sum of the differences (squared) between the target values and the values obtained for the different criteria and by associating with each term a coefficient representing its importance in computing the cost function, and/or
  by setting tolerances around a given optical function, defining a range of optical functions in which a solution amending criterion flow and/or the power profile may be selected.

As indicated previously, the method of the invention may be implemented having the wearer carry out the locomotion scenario in the real word using different ophthalmic lenses with different optical functions.

However, the method of the invention may further be implemented using a virtual locomotion scenario and having virtual ophthalmic lenses provided to the wearer.

The invention may also be implemented on a virtual wearer having the main features of the real wearer to determine the most appropriate ophthalmic lens for the wearer.

Furthermore, the method of the invention may be used to determine an optical design of an ophthalmic lens to be manufactured or an optical design to be applied be sent to an optical lens controller controlling a programmable lens.

An example a programmable lens device whose optical function can be modified is disclosed in WO2015014910.

Typically, a programmable ophthalmic lens comprises a transparent set of electroactive cells juxtaposed parallel to a surface of the lens. The set of cells is suitable for providing an optical phase-shift distribution function with a substantially constant value within each cell.

Preferably, each cell is filled with an active electro-material such that the refraction index can vary in each pixel independently from each other under the action of an electric field induced by individual electrodes.

The device can be disposed on a face of the transparent set of electroactive cells facing the eye.

Of course, the programmable lens device comprises a device adapted to provide the adapted electric field.

It is well-known of the man skilled in the art methods to manufacture pixelated ophthalmic lenses having unspecified surfaces.

The method of the invention may allow adapting the optical function of a programmable optical lens to a locomotion parameter of the user. For example, upon detection or input from the wearer that said wearer is walking the optical function may be adapted based on a locomotion parameter.

The invention has been described above with the aid of embodiments without limitation of the general inventive concept.

Many further modifications and variations will suggest themselves to those skilled in the art upon making reference to the foregoing illustrative embodiments, which are given by way of example only and which are not intended to limit the scope of the invention, that being determined solely by the appended claims.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used. Any reference signs in the claims should not be construed as limiting the scope of the invention.

The invention claimed is:

1. A method for determining an ophthalmic lens adapted to a wearer, the method comprising:
    obtaining, by processing circuitry, wearer data comprising at least an indication of a prescription of the wearer;
    obtaining, by the processing circuitry, a locomotion scenario, the locomotion scenario comprising at least an input locomotion parameter and visual environment data indicative of a visual environment, the locomotion parameter comprising at least movement data indicative of at least a translation movement of a head of the wearer upon movement in the visual environment;
    obtaining, by the processing circuitry, a target value of an output parameter, the output parameter being a locomotion parameter of the wearer or an optical parameter of the ophthalmic lens having an impact on a locomotion parameter of the wearer; and
    determining, by the processing circuitry, an ophthalmic lens adapted to the wearer based at least on the wearer data to have the output parameter as close as possible to the target value of the output parameter when carrying out the locomotion scenario using the ophthalmic lens,
    wherein the output parameter is retinal flow of the wearer when carrying out the locomotion scenario using the ophthalmic lens, the retinal flow corresponding to a projection of optical flow, which corresponds to optical changes produced by the movement of the head of the wearer and the rotation of the eyes of the wearer in orbits of the eyes, in retinal coordinates on a receiving surface, and
    wherein the retinal flow is a vector field defined by the optic flow projected through the lens in the entire retina surface on the central and peripheral part of the retina.

2. The method according to claim 1, wherein the input locomotion parameter is a parameter of the wearer when carrying out the locomotion scenario using the ophthalmic lens.

3. The method according to claim 2, wherein the locomotion parameter is trajectory and/or speed and/or direction and/or movements of any part of a body, when carrying out the locomotion scenario using the ophthalmic lens.

4. The method according to claim 1, wherein the ophthalmic lens comprises a zone of optical interest and during the ophthalmic lens determining an optical function of at least a first part of the zone of optical interest is determined based at least on the output parameter and the prescription of the wearer.

5. The method according to claim 4, wherein dimensions and/or position of the first part of the zone of optical interest are determined based on the locomotion scenario and/or wearer personalization data indicative of at least to age and/or morphology and/or sensory motor state of the wearer.

6. The method according to claim 1, wherein the determining further comprises selecting an optical function in a list of at least two optical functions, the optical function being selected based at least on the wearer data.

7. The method according to claim 1, wherein the wearer data further comprises a troubling output parameter and during the determining an optical function is selected to minimize the troubling output parameter when carrying out the locomotion scenario using the ophthalmic lens.

8. The method according to claim 1, wherein the locomotion parameter of the wearer is measured using a sensing device carried by the wearer upon movement in the visual environment.

9. The method according to claim 1, wherein the determining further comprises determining a geometrical parameter of the ophthalmic lens, the geometrical parameter being determined based at least on the wearer data.

10. The method according to claim 1, wherein the determining further comprises:
    obtaining a set of parameters of the ophthalmic lens, the set of parameter comprising at least an output parameter of the wearer when carrying out a locomotion scenario using the ophthalmic lens; and
    obtaining, for each parameter of the set of parameter, a cost function, wherein the ophthalmic lens is determined to minimize the global cost function, the global cost function being a weighted sum of the cost functions used to optimize output parameters during ophthalmic lens design.

11. The method according to claim 1, wherein the visual environment and the ophthalmic lens are virtually simulated by a computer.

12. The method according to claim 11, wherein the wearer is virtually simulated by the computer.

13. A non-transitory computer readable medium including a computer program product comprising one or more stored sequences of instructions that are accessible to a processor and which, when executed by the processor, causes the processor to carry out the method according to claim 1.

14. An apparatus for determining an ophthalmic lens adapted to a wearer, the apparatus comprising:
    processing circuitry configured to:
        obtain wearer data comprising at least an indication of a prescription of the wearer, obtain a locomotion scenario, the locomotion scenario comprising at least an input locomotion parameter and visual environment data indicative of a visual environment, the locomotion parameter comprising at least movement data indicative of at least a translation movement of a head of the wearer upon movement in the visual environment, obtain a target value of an output parameter, the output parameter being a locomotion parameter of the wearer or an optical parameter of the ophthalmic lens having an impact on a locomotion parameter of the wearer, and determine an ophthalmic lens adapted to the wearer based at least on the wearer data to have the output parameter as close as possible to the target value of the output parameter when carrying out the locomotion scenario using the ophthalmic lens, wherein the output parameter is retinal flow of the wearer when carrying out the locomotion scenario using the ophthalmic lens, the retinal flow corresponding to a projection of optical flow, which corresponds to optical changes produced by the movement of the head of the wearer and the rotation of the eyes of the wearer in orbits of the eyes, in retinal coordinates on a receiving surface, and wherein the retinal flow is a vector field defined by the optic flow projected through the lens in the entire retina surface on the central and peripheral part of the retina.

* * * * *